United States Patent

Hertha

[11] Patent Number: 5,907,116
[45] Date of Patent: May 25, 1999

[54] METHOD AND DEVICE FOR REPRODUCING A STARLIT SKY

[76] Inventor: Kurt Hertha, Heckenrosenstr. 2, 82031 Gruenwald, Germany

[21] Appl. No.: 08/759,627

[22] Filed: Dec. 5, 1996

[30] Foreign Application Priority Data

Dec. 8, 1995 [DE] Germany .............................. 195 45 939

[51] Int. Cl.[6] .................................................. G10H 7/00
[52] U.S. Cl. ............................. 84/600; 84/464 R; 353/62; 434/289
[58] Field of Search ................................ 84/600; 353/15, 353/62; 359/444; 434/285–287, 289

[56] References Cited

U.S. PATENT DOCUMENTS

| | | |
|---|---|---|
| 3,473,428 | 10/1969 | Phillips . |
| 4,045,885 | 9/1977 | Stern . |
| 4,858,079 | 8/1989 | Ohashi ................................. 353/62 X |
| 5,007,707 | 4/1991 | Bertagni . |
| 5,097,326 | 3/1992 | Meijer ..................................... 358/94 |
| 5,310,962 | 5/1994 | Kimpara et al. ......................... 84/600 |
| 5,492,475 | 2/1996 | Hatori ..................................... 434/286 |

*Primary Examiner*—William M. Shoop, Jr.
*Assistant Examiner*—Jeffrey W. Donels
*Attorney, Agent, or Firm*—Griffin, Butler, Whisenhunt & Szipl, LLP

[57] ABSTRACT

A process for the reproduction of a starlit sky involves accompanying stars and other space bodies with acoustical tones corresponding to their optical images. Particularly individual spectral classes of the stars will each be assigned to an octave of music. The invention also includes combining a device with a telescope for providing acoustical reproduction of respectively observed stars and space bodies.

8 Claims, 9 Drawing Sheets

METHOD AND DEVICE FOR REPRODUCING A STARLIT SKY

BACKGROUND OF THE INVENTION

This invention concerns methods and apparatus for observing space bodies, particularly planetariums and telescopes.

Planetariums are well known for reproducing starlit skies in which the heavenly bodies and their position changes relative to one another are made visible on a dome. In order to do this, the starlit sky can be reproduced by optical projection on an interior surface of the dome, see, FIG. 7. Visually impaired people can only perceive this optical reproduction of a starlight sky to a limited extent and an impression of a starlit sky cannot be communicated at all to blind people with such an apparatus.

It is an object of this invention to provide a method and an apparatus for reproducing a starlit sky which is structured so that its optical visibility is reinforced and an impression of the starlit sky can be communicated to blind people.

SUMMARY OF THE INVENTION

According to principles of this invention, the stars which have different optical images have different tones associated therewith. For example, by associating higher musical tones to bright, blue radiating stars and deeper tones to darker, red radiating stars an optical impression of a viewing of a star group in a planetarium can be reinforced, while the acoustical reproduction by itself opens the possibility for blind people to receive an impression of a starlit sky.

Preferably, each of the seven spectral groups in which the individual stars are arranged in astronomy are respectively associated with, or accompanied by, one of the seven octaves of music.

BRIEF DESCRIPTION OF THE DRAWING

The invention is described and explained in more detail below using the embodiments shown in the drawings. The described and drawn features, in other embodiments of the invention, can be used individually or in preferred combinations. The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DESCRIPTION OF THE PREFERRED EMBODIMENT

Figure 1A:
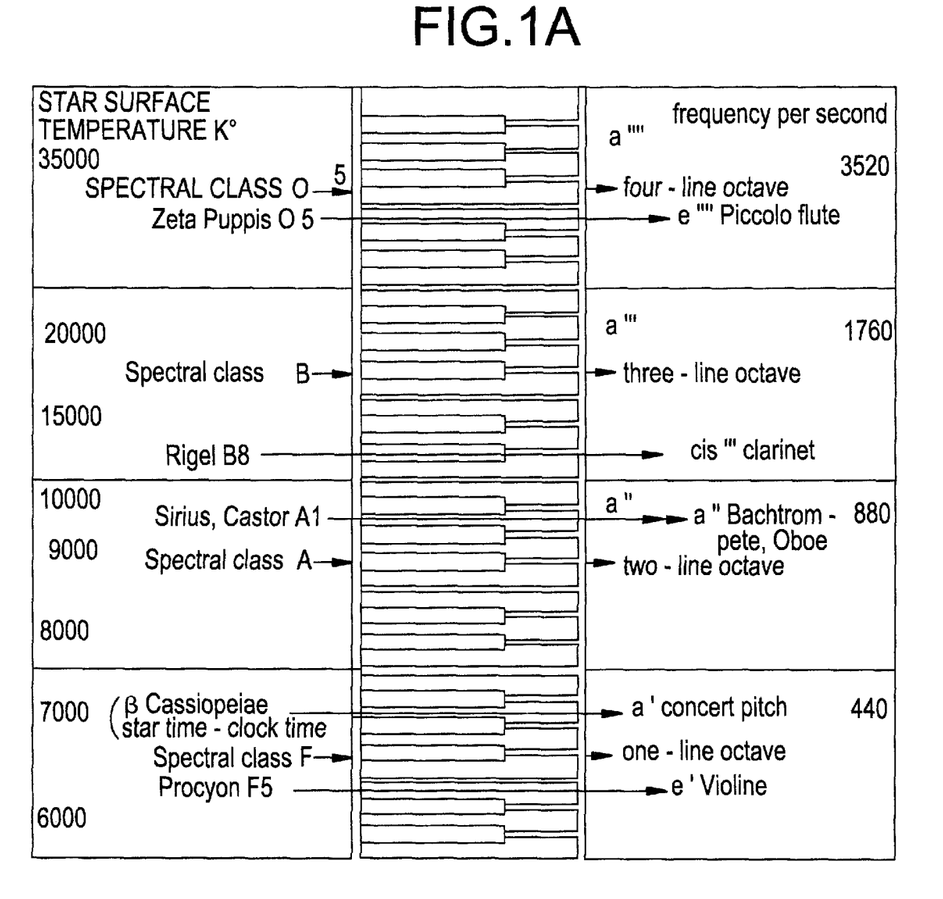
FIGS. 1A and 1B are diagrammatic views showing a division of the various spectral classes of stars for each of which respectively an octave of music is associated.
Figure 1B:
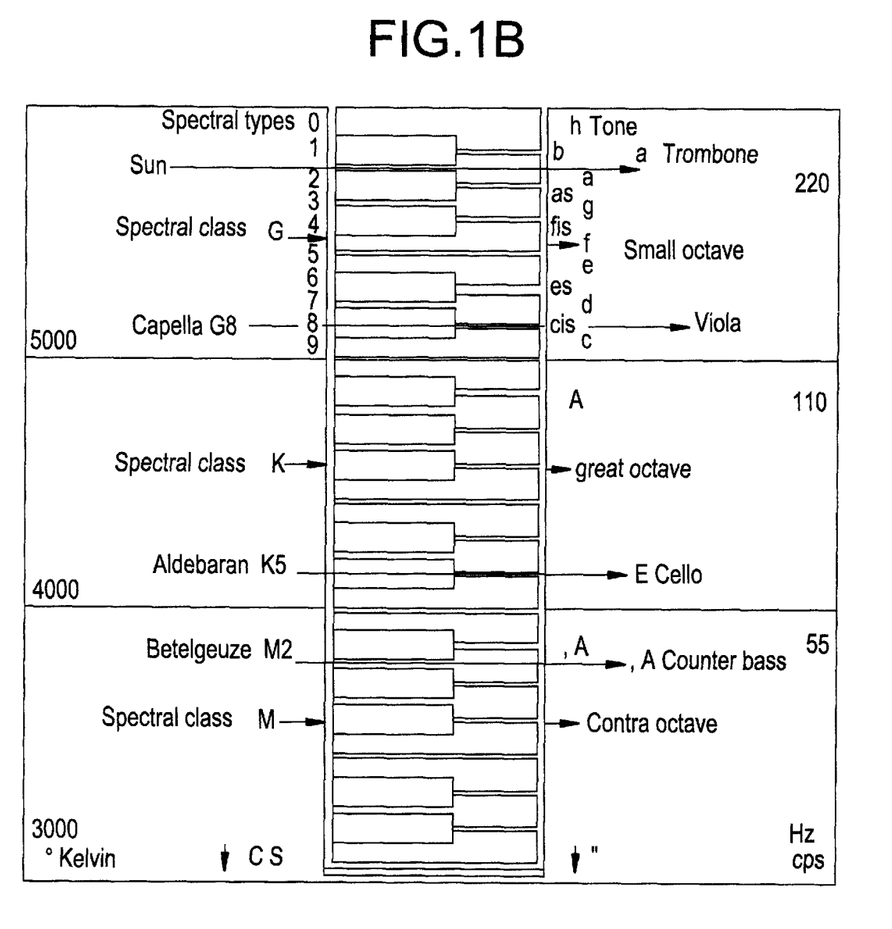

In FIGS. 1A and 1B, a division of the stars into seven spectral classes is provided in the left column, while a respective one of the seven octaves of music associated with each is provided in the right column. In the left column, the corresponding star surface temperatures °K are provided in each of the spectral classes and in the right column the corresponding tone frequencies in Hz are provided. In the middle column, in order to clarify the resulting tones, a piano keyboard is shown. According to this, blue radiating stars of the spectral class O have the higher tones of the four-line octave, the spectral class B the three-line octave, the spectral class A the two-line octave, the spectral class F the one-line octave, the spectral class G the small octave, the spectral class K the great octave, and the spectral class M the contra octave. As examples, individual stars with their astronomical identifications are given in the left column, while a respective corresponding tone assigned thereto is indicated by an arrow pointing into the right column.

Preferably, the individual tones are reproduced by various instruments, as is indicated in the right column, whereby, for example, the four-line octave e (designated in FIGS. 1A and 1B as e"", the primes representing the octave) is reproduced by a piccolo flute and the one-line e (e' in the diagram) is reproduced by a violin.

Figure 2:
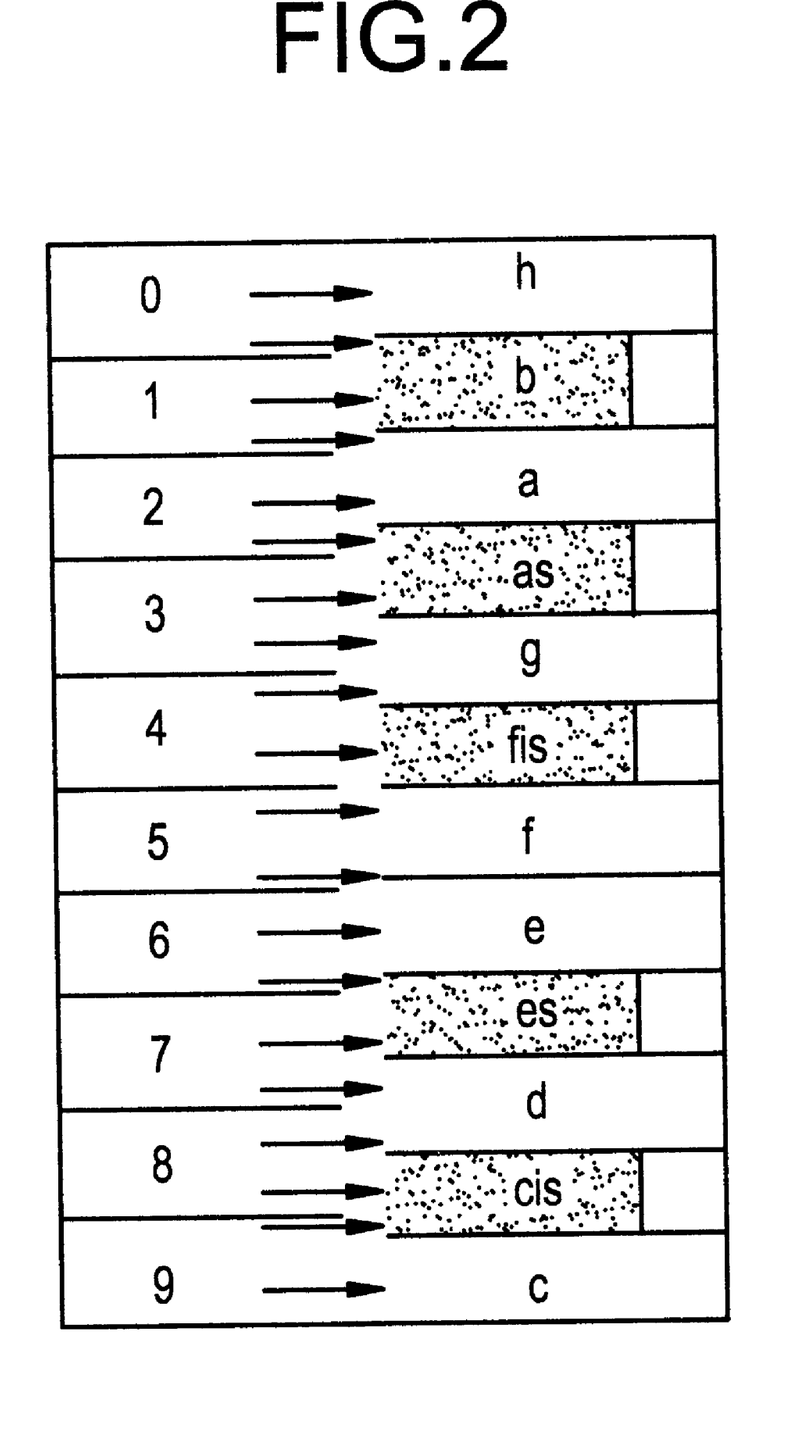
FIG. 2 is a diagrammatic representation of a reproduction of the transition of 10 spectral types to twelve halftones.

Spectral types 0–9 are provided in the spectral class G which correspond to the individual tones h to c which can be seen more clearly in FIG. 2. The spectral type determines the tone, whereby, for example, in the case of the spectral type G6 two possibilities in the form of e and es (e flat) are available, as is shown in FIG. 2. The conversion of the ten spectral types into the twelve half tones includes with it that for the acoustical reproduction of each star there are two possibilities available. This is true for all spectral classes for all of the octaves. In individual cases:

Spectral types 0=h or b
    1=b or a
    2=a or as
    3=g or as
    4=fis or g
    5=f or e
    6=e or es (e flat)
    7=d or es
    8=cis or d
    9=or cis (c sharp)

The brightness of the individual stars can be simulated in the form of loud-speaker amplification of the accompanying tones, whereby the large classes 1m to 6m of the stars can be associated with dynamic representations f–p (forte (loud) to piano (soft)) according to the following table:

0–1m=f (loud)
    1–2m=mf (medium loud)
    2–3m=mp (medium faint)
    3–4 m=p (soft)
    4–5m=pp (very soft)
    5–6m=(faint)

If, for example, individual galaxies or stars are optically reproduced to have ocular amplification, the optically enlarged reproduction is accompanied by a corresponding acoustical tone amplification.

Figure 3A:
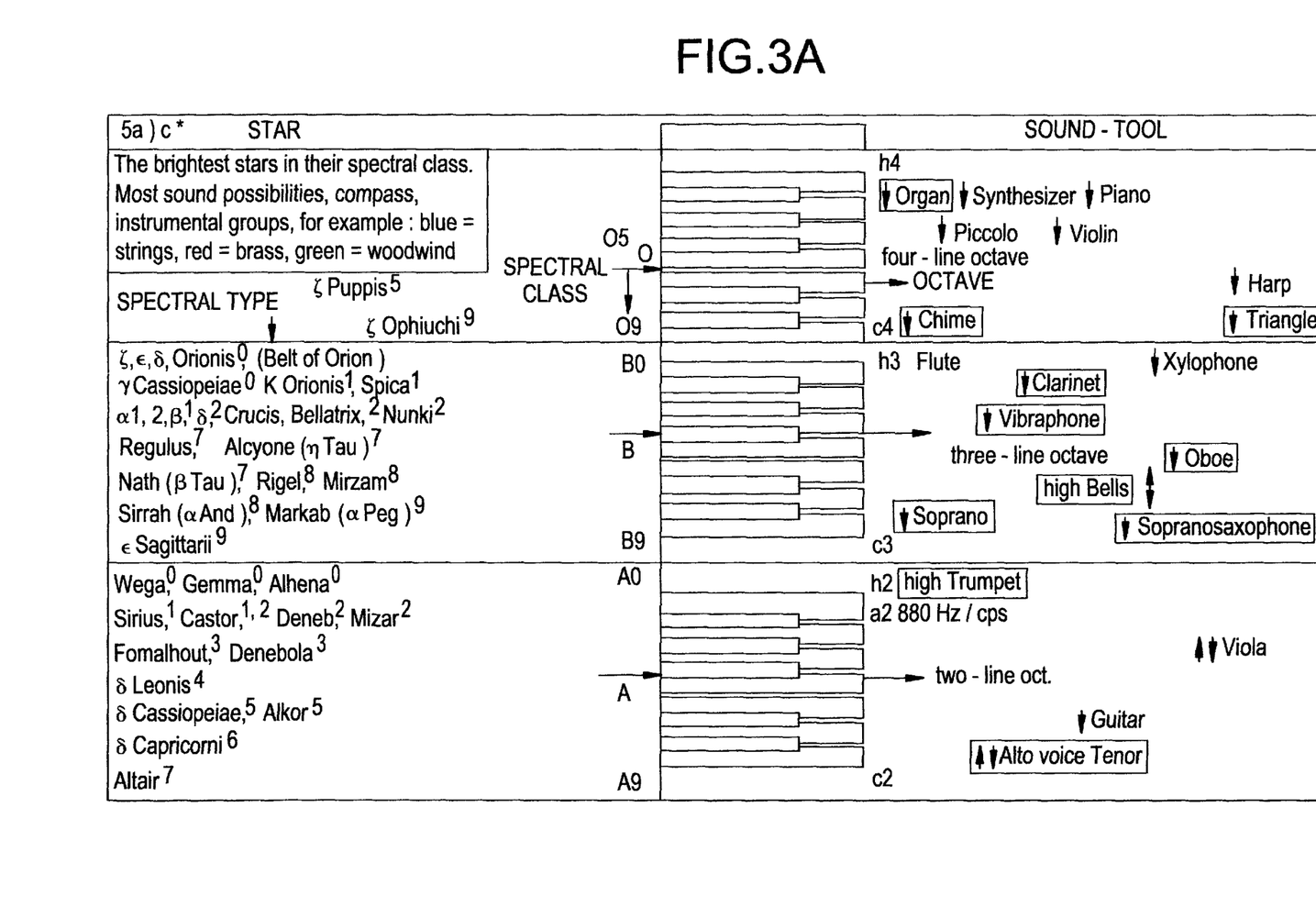
FIG. 3A, FIG. 3B, and FIG. 3C are diagrammatic representations similar to the diagrams of FIG. 1A and FIG. 1B showing the division in further detail.
Figure 3B:
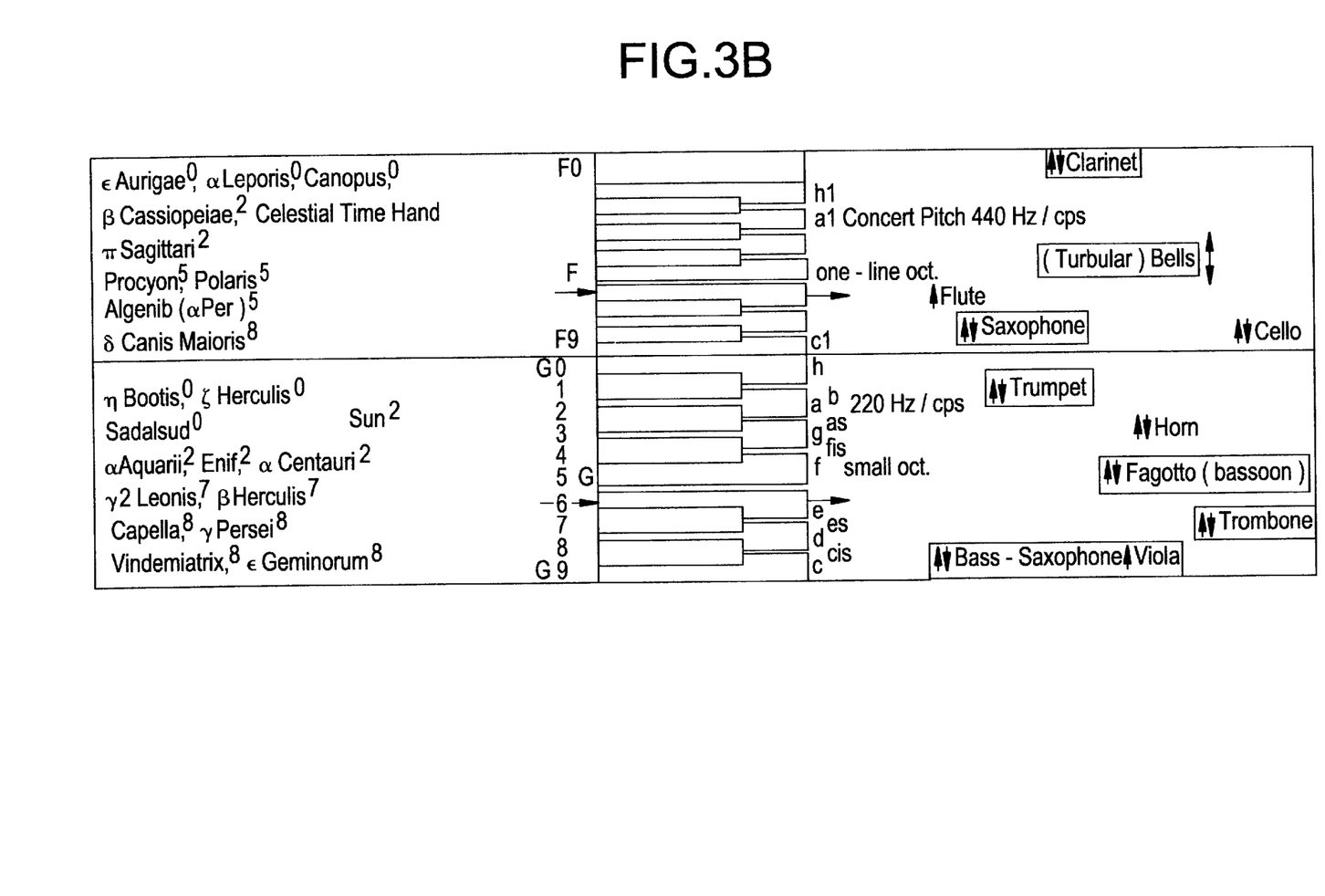
Figure 3C:
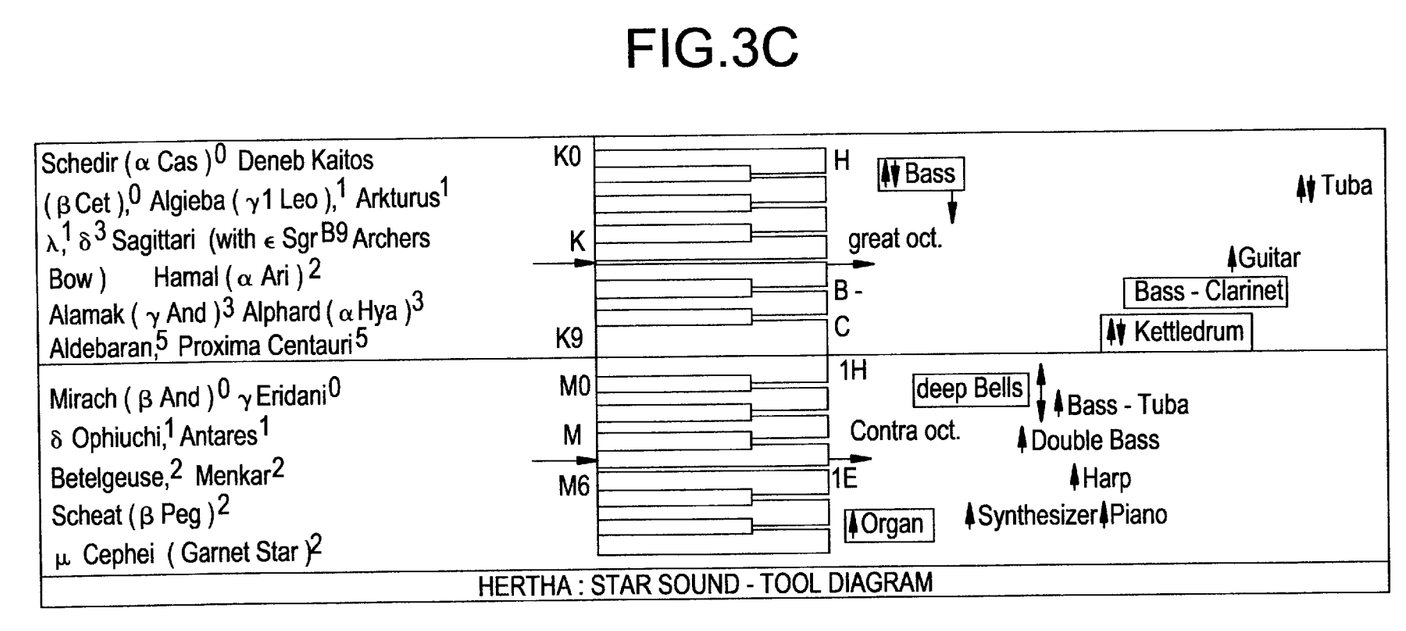

As already indicated in FIGS. 1A and 1B, the individual high or deep, loud or soft, tones are preferably acoustically reproduced by musical instruments. Possibilities for this are shown in FIGS. 3A, 3B, and C in which the large stars are shown in their respective spectral classes in the left column and their respectively associated, or accompanying, instruments are provided in the right column. In this, the guitar can, for example, be employed from the great octave to the two-line octave, as is indicated by vertically-directed arrows in the right column adjacent corresponding instrument names.

When, at the most, a star group can be respectively perceived with eyes, also only individual star groups, or also only individual stars, will be reproduced acoustically when they are respectively pointed out in a planetarium to be viewed. In a star group each individual star can, for example be accompanied by a different instrument. When this is done, various combination possibilities exist.

Figure 4:
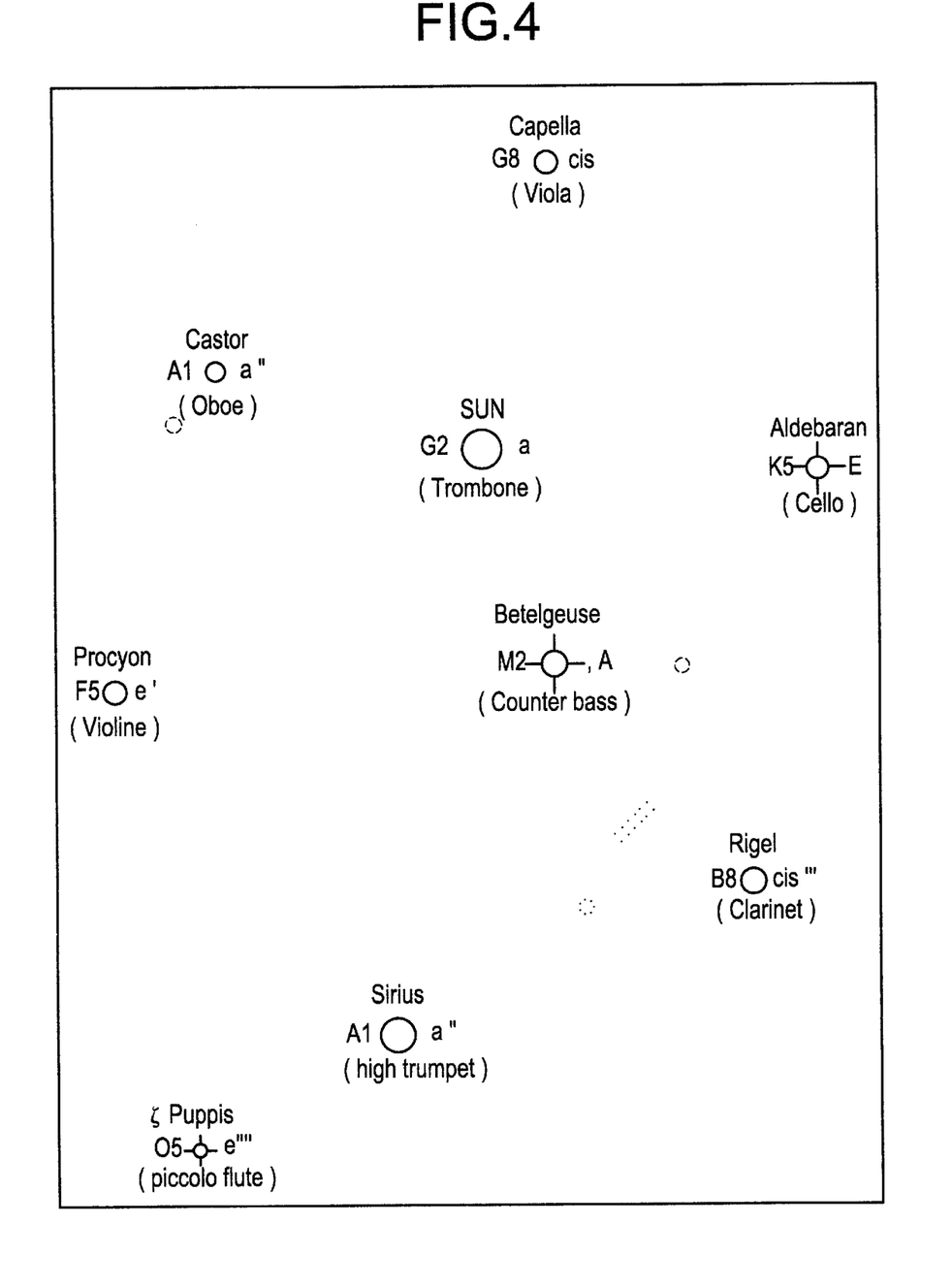
FIG. 4 is a schematic diagrammatic view of a star group showing an assignment of associated tones.

FIG. 4 shows schematically a star group of the winter hexagon with sun. The winter hexagon with Betelgeuse and Zeta puppis exhibits in eight stars all seven spectral classes so that the acoustic reproduction of all seven octaves is required. A spectral type on the left for each individual star is respectively accompanied by the tone which is given on the right, as can be seen in FIGS. 1A, 1B, 3A, 3B and 3C. When this is done, a pleasing sounding A major chord is achieved.

Figure 5:
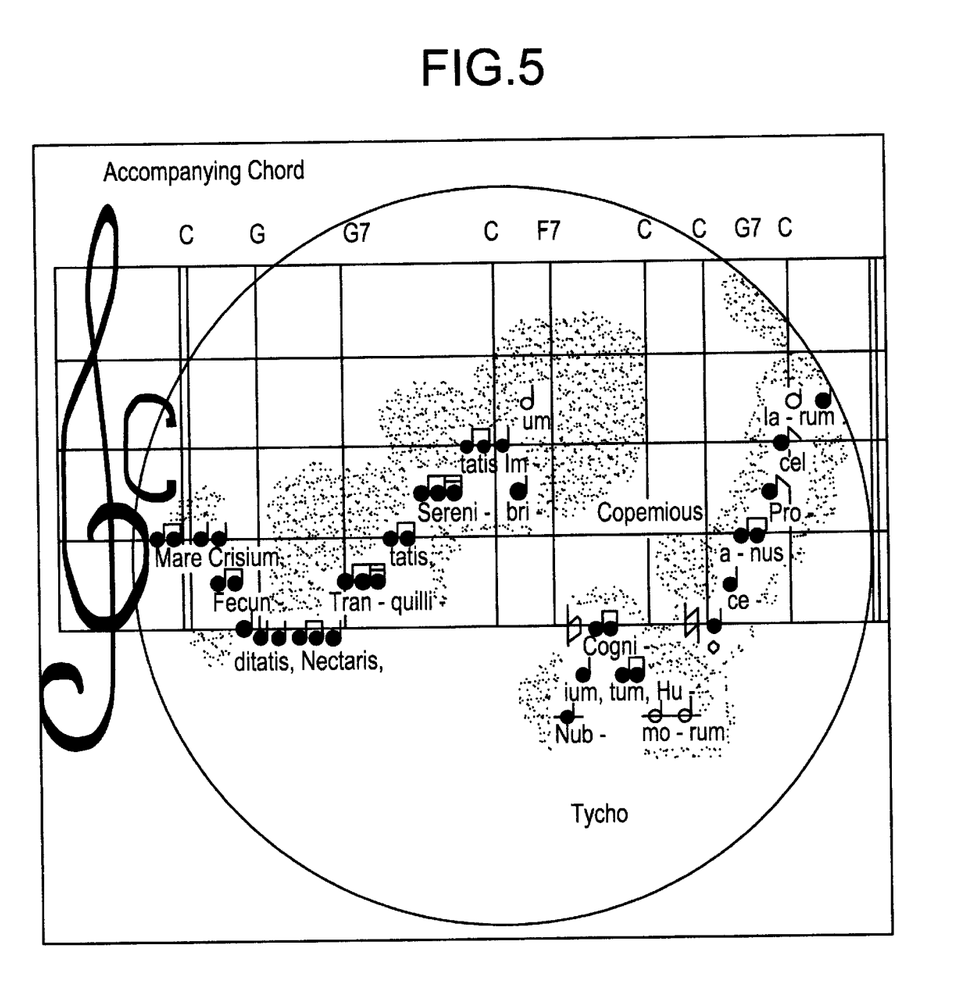
FIG. 5 is a diagrammatic representation of an acoustical reproduction of an individual heavenly body, such as that of the moon.

FIG. 5 is a diagram of an acoustical reproduction of an individual heavenly body, such as the moon in which the individual Mariae (or moon seas), as they are represented in FIG. 5 by their respective names, are associated with tone groups, or chords. In FIG. 5 the important Mariae are reproduced on note lines, or sheet-music lines, as coordinates. In this embodiment, a heavenly body is not accompanied by a single tone rather its surface configuration is reproduced by various different tones of the loudspeaker system distributively reproduced.

Figure 6:
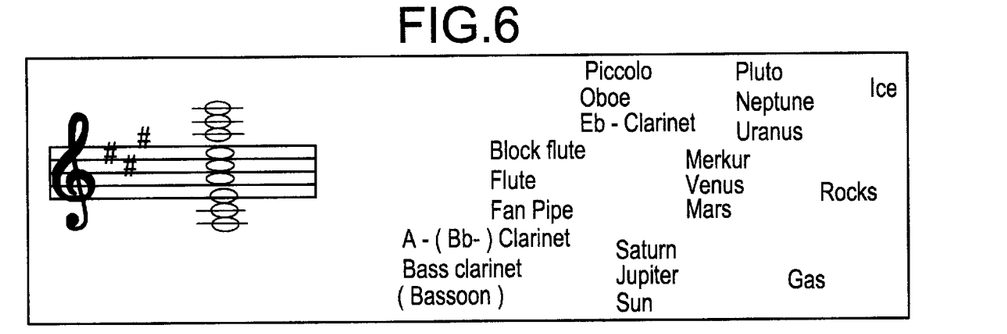
FIG. 6 is a diagrammatic representation of an acoustical reproduction of a planet system, or solar system.

For the reproduction of our planet system, the following individual heavenly-body tones will be assigned as follows:

|         |                            |
|---------|----------------------------|
| Sun     | a                          |
| Jupiter | cis' (c sharp, one-line octave) |
| Saturn  | e'                         |
| Mars    | a'                         |
| Venus   | cis" (c sharp, two-line octave) |
| Mercury | e"                         |
| Uranus  | a"                         |
| Neptune | cis'"                      |
| Pluto   | e'".                       |

FIG. 6 shows these assignments along with the instruments which, according to the suggestion made in FIG. 3, are employed. The individual members of the planet system are divided into three groups according to their principal structures "gas, rock, ice".

If, for example, the moon in its orbit is reproduced in a planetarium in association with a starlit sky, an acoustical reproduction can be made in such a manner that a tone assigned to the moon drowns out all tones which are assigned to stars over which the moon momentarily passes in its orbit.

Figure 7:
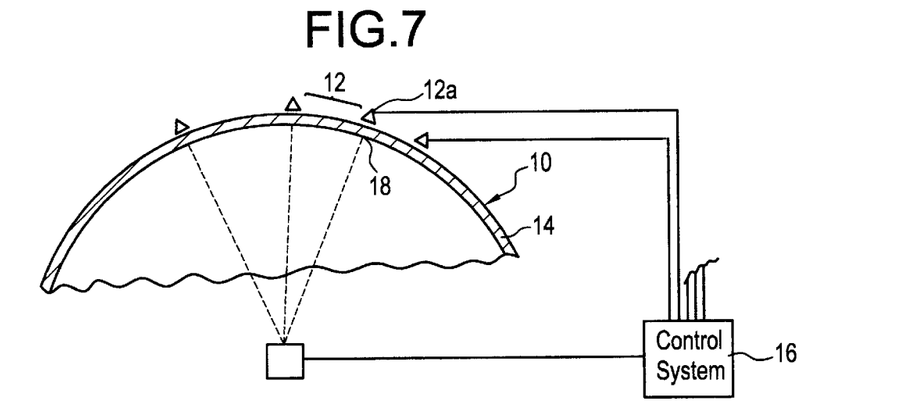
FIG. 7 is a partially cross-sectional, schematic block diagram of a first-embodiment system of this invention.

For the acoustical reproduction of the starlit sky in a planetarium 10, loud speakers 12 are distributed on an exterior side of an acoustically transparent projection dome 14. These can be so controlled by an appropriate circuit from a control system 16 that a loud speaker 12a whose position is substantially the same on the projection dome as an optically projected star 18, which should also be made acoustically recognizable, reproduces the assigned tone for the star. The control system preferably includes a computer which has a corresponding program which assigns corresponding tones for the stars projected by the projecting system and controls the appropriate loud speakers.

In this manner movement of the individual heavenly bodies over the projection dome 14 can be acoustically reproduced by activating loud speakers, one after the other, to produce the respective tones along the orbits of the appropriate heavenly bodies.

Figure 8:
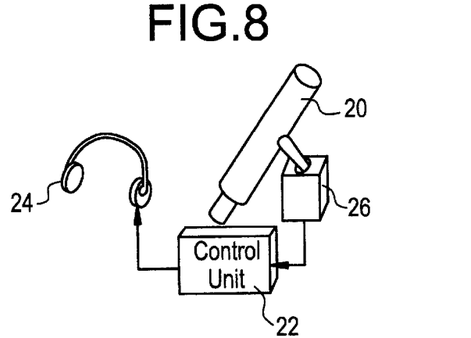
FIG. 8 is a schematic diagram of a second-embodiment of this invention.

According to a further embodiment (FIG. 8) of the invention, a telescope 20, as is used for observing stars, is provided with an electronic control unit 22, with which the respectively observed stars or star groups are assigned predetermined tones which are acoustically reproduced by a loud speaker or headphones 24. This is particularly suitable for telescopes which are outfitted with an electronic positioning unit 26 for locating individual stars or particular space directions. The electronic control unit for acoustically reproducing the stars can be integrated into such a positioning unit for alignment of the telescope or combined therewith.

Figure 9:
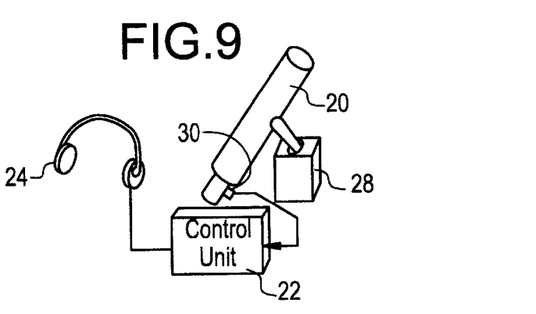
FIG. 9 is a schematic diagram of a third-embodiment of this invention.

In another embodiment (FIG. 9) of the invention, a telescope having an electronic control unit, such as an auto-guider 28, is provided with a device 30 which analyzes light from stars received through the telescope and which separates it into the respective spectral classes and spectral types; and, for example according to the arrangement of FIGS. 1A and 1B, tones are assigned to the received light, which tones are electronically created and reproduced over loud speakers or headphones. By means of such an apparatus, for example, a star upon which a telescope is aimed and which, over a long time, displays different light spectrums, can be monitored and observed such that one must initially only listen to a tone which changes in accordance with the changes in the spectrum of the received light, but when the light changes, one is alerted thereto by the changing tone, and can then also optically observe the star through the telescope. Such an apparatus for converting the received light into acoustical tones can also be provided for a telescope without an auto-guider.

Figure 10:
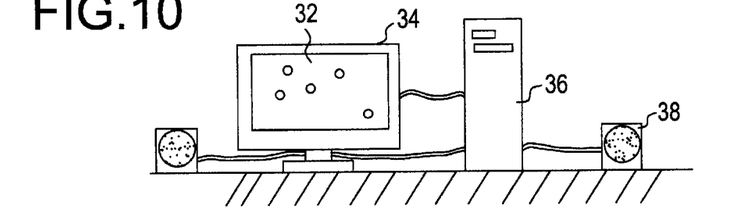
FIG. 10 is a schematic diagram of a fourth-embodiment of this invention.

According to a further embodiment (FIG. 10) of the invention, the starlit sky can be optically shown on a monitor 34 of a computer 36 in a frame cut-out fashion whereby sound tones assigned to respectively observed stars or star groups can be reproduced at 38. Also in this embodiment, preferably, a tone program, indicated schematically in FIG. 10 by reference number 40, is integrated into, or combined with, an optical program, indicated schematically in FIG. 10 by reference number 42, to optically reproduce star images or individual space bodies so that tones which are assigned to observed stars are acoustically reproduced, preferably, the tone assignments being in accordance with FIGS. 1–5.

The described acoustic reproduction of stars or star groups can be termed astrophonie in accordance with an assignment of acoustical tones to the astronomical division of stars.

The invention claimed is:

1. Process for reproducing a starlit sky comprising the steps of: controlling an optical device so as to produce optical images of a plurality of stars of the starlit sky; assigning a corresponding acoustical tone to each produced optical image, wherein each acoustical tone has a characteristic related to a spectral class of a star to whose optical image the tone is assigned, with the acoustical tone being in a different octave of music than acoustical tones assigned to other optical images, the respective octaves of the acoustical tones depending on the respective spectral classes of the stars to whose optical images the acoustical tones are assigned; and producing the acoustical tones when the respective optical images to which they are assigned are produced.

2. Process as in claim 1 wherein the optical images of ten spectral types of stars in one spectral class are assigned twelve half tones of a single octave with each optical image being assigned two adjacent half tones.

3. Process as in claim 1 wherein the acoustical tones assigned to optical images for brighter glowing stars are louder tones than acoustical tones assigned to optical images of weaker glowing stars.

4. Process as in claim 1 wherein acoustical tones assigned to optical images of different stars are respectively tones of different musical instruments.

5. Apparatus for the reproduction of a starlit sky on a projection dome on which stars are reproduced as star images by optical projections, said apparatus comprising:

a projection dome constructed as an acoustically transparent member;

a means for projecting said star images on the interior of the projection dome;

spaced speakers arranged on an exterior surface of the projection dome; and a control unit coupled to the speakers for electronically controlling the speakers to cause the speakers to produce acoustical tones assigned to reproduced stars whose star images are at the respective speakers, with each of the tones having different characteristics from those of other tones produced by other speakers located at other star images of reproduced stars, each tone having characteristics related to a star whose star image is at the respective speaker causing the tone.

6. Apparatus for acoustically reproducing optical images of stars a starlit sky comprising:

a telescope for creating observable optical images at a telescope eyepiece thereof of stars toward which said telescope is directed in a natural starlit sky;

an electric positioning unit for aiming the telescope at particular stars in the natural starlit sky; and an electronic control device, including a speaker, coupled to the electronic positioning unit for assigning respective different acoustical tones to each of the particular stars located in the natural starlit sky and for respectively reproducing each of these assigned acoustical tones on the speaker when the positioning unit directs the telescope toward the star to which the respective tone is assigned by the control device to thereby create on observable optical image at said telescope eyepiece of the star toward which said telescope is directed.

7. Apparatus for acoustically reproducing a starlit sky comprising;

a telescope for creating an observable optical image at a telescope eyepiece thereof of stars toward which said telescope is directed in a natural starlit sky by receiving light from the natural starlit sky;

a device attached to the telescope for analyzing the light received by the telescope from respective stars toward which said telescope is directed and for creating acoustical tones corresponding to the analyzed light, whereby said device creates different tones for stars for which different light is received, but reproduces tones with similar characteristics for stars from which similar light is received.

8. Apparatus for acoustically reproducing a starlit sky comprising:

a monitor;

controlling means for controlling the monitor to optically display portions of the sky, including stars;

assigning means for assigning different acoustical tones to the respectively displayed stars, with the tones being in different octaves for stars in different spectral classes, there being a different octave for each spectral class; and speaker means for playing these respective tones when the stars to which these tones are assigned are displayed.

* * * * *